US006807769B2

(12) United States Patent
Bish et al.

(10) Patent No.: US 6,807,769 B2
(45) Date of Patent: Oct. 26, 2004

(54) STRAWBERRY TRANSPLANT CONDITIONING FOR FLOWERING INDUCTION

(75) Inventors: Eric B. Bish, New Hill, NC (US); Daniel J. Cantliffe, Gainesville, FL (US); Craig K. Chandler, Tampa, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/172,689

(22) Filed: Oct. 14, 1998

(65) Prior Publication Data

US 2003/0182856 A1 Oct. 2, 2003

(Under 37 CFR 1.47)

Related U.S. Application Data

(60) Provisional application No. 60/061,969, filed on Oct. 14, 1997.

(51) Int. Cl.$^7$ .......................... A01B 79/00; A01B 79/02; A01C 1/00; A01G 1/00; A01H 3/00
(52) U.S. Cl. ....................................................... 47/58.1
(58) Field of Search .......................................... 47/58.1

(56) References Cited

U.S. PATENT DOCUMENTS 5,444,179 A * 8/1995 Izhar et al.

OTHER PUBLICATIONS

Heide, O. M., "Photoperiod and Temperature Interactions in Growth and Flowering of Strawberry," The Scandinavian Society for Plant Physiology, vol. 40 (1): 21–26, 1977.*
Sonsteby, A., "Short–Day Period and Temperature Interactions on Growth and Flowering of Strawberry," Third International Strawberry Symposium vol. II, Acta Horticulturae, No. 439, pp. 609–616, Sep. 1997.*
Darrow, G.M., "The Strawberry", 1966, Holt, Rinehart and Winston, pp. 355–365.*
Long, J.H. (1935) "Seasonal changes in nitrogen and carbohydrate content of the strawberry plant" Proc. Amer. Soc. Hort. Sci. 33:386–388.
Durner, Edward F. and E. Barclay Poling (1986) "Early Season Yield Responses of Selected Strawberry Cultivars to Photoperiod and Chilling in a Florida Winter Production System" J. Amer. Soc. Hort. Sci. 111(6):53–56.

Durner, Edward F., J.A. Barden, D.G. Himelrick, E.B. Poling (1984) "Photoperiod and Temperature Effects on Flower and Runner Development in Day–Neutral, Hunebearing, and Everbearing Strawberries" J. Amer. Soc. Hort. Sci. 109(3):396–400.
Smith, Scott A. and Timothy G. Taylor (Jun., 1991) "Production Costs for Selected Vegetables in Florida, 1990–91" Economic Information Report EI 91–2 (Food & Resource Economics Dept., Agr. Exp. Stations, IFAS, University of Florida, Gainesville, FL 32611).
Bish, E.B. et al. "Development of containerized strawberry transplants for Florida's winter production system" Acta Hort., 1997, book No. 439, vol. 1, pp. 461–468.
Bish, E.B. et al. "A system for producing large quantities of greenhouse–grown strawberry plantlets for plug production" HortTechnology, 2001, 11(4):636–638.
Bish, E.B. and Cantliffe, D.J. "Strawberry daughter plant size alters transplant growth and development" Acta Hort., 2000, book No. 533, vol. 1, pp. 121–124.
Bish, E.B. et al. "Container volume and media particle size alter growth of strawberry transplants" Proc. Fla. State Hort. Soc., 1997, 110:258–261.
Bish, E.B. et al. "Strawberry plug transplants: Regulation of growth and production" Proc. Fla. State Hort. Soc., 1996, 109:160–164.
Bish, E.B. et al. "Temperature conditioning and container size affect early season fruit yield of strawberry plug plants in a winter, annual hill production system" HortScience, 2002, 37(5):762–764.
Darnell, R.L. et al. "The physiology of flowering in strawberry" Horticultural Reviews, 2003, 28:325–349.
Kirschbaum, D.S. et al. "Strawberry waiting bed plants: a valid alternative to increase early and total yields in subtropical regions" Scientia Horticulturae, 2000, 84:83–90.
Kirschbaum, D.S. et al. "Propagation site latitude influences initial carbohydrate concentration and partitioning, growth, and fruiting of 'Sweet Charlie' strawberry (Fragaria X Ananassa Duch.) transplants grown in Florida" Proc. Fla. State Hort. Soc., 1998, 111:93–96.

* cited by examiner

Primary Examiner—Bruce R. Campell
Assistant Examiner—S. B. McCormick-Ewoldt
(74) Attorney, Agent, or Firm—Saliwanchik, Lloyd & Saliwanchik

(57) ABSTRACT

The subject invention concerns a process for enhancing flower induction in strawberry plants by artificial means. The process comprises exposing the strawberry plants to reduced daylight temperatures and/or reduced daylight after the strawberry plant is grown for a period of time at a high temperature which temperature does not permit flowering.

16 Claims, No Drawings

STRAWBERRY TRANSPLANT CONDITIONING FOR FLOWERING INDUCTION

CROSS-REFERENCE TO RELATED APPLICATIONS

This application claims the benefit of the filing date of U.S. Provisional Application Ser. No. 60/061,969 filed Oct. 14, 1997.

BACKGROUND OF THE INVENTION

Strawberries are an important and valuable crop throughout the world. Due to genetic heterozygosity, adaptability, and plasticity of the plant, this species can grow in varied environments throughout the world, from Alaska to South Africa (Martinelli, A. [1992] "Micropropagation of strawberry (Fragaria spp.)" In: Biotechnology in Agriculture and Forestry 18:354–370, Springer Verlag, Berlin, W. Germany). The high value of the fruit allows for intensive production methods in many regions.

Florida produced approximately 75 million kilograms of strawberries on 2,350 hectares in the 1993–94 season, an average yield of over 32,000 kg ha$^{-1}$ (Freie, R. and N. Pugh [1995] Florida agricultural statistics: Vegetable Summary 1992–1993, Florida Department of Agriculture and Consumer Services, Tallahassee, Fla. p. 47–48). Most of the crop is harvested between December and April with peak production occurring in mid-March. The average value of fruit ranged from greater than $3.00 per kg in November/December declining through the season to less than $1.00 per kg in March/April. However, only 10% of Florida's strawberry production occurs in November/December when the crop value is highest. Greater than 50% of Florida's production occurs in March/April when fruit value is below production costs (Smith, S. and T. Taylor [1993] "Production cost for selected vegetables in Florida, 1992–93," In: *University of Florida Circular* 1121, Gainesville, Fla. p.22).

Commercial strawberry cultivars must be vegetatively propagated because seeds are not true to type. This propagation has traditionally been done in field nurseries to produce a bare-root transplant. There are many problems associated with these bare-root transplants. However, containerized transplants also have drawbacks including being very vegetative and lacking early fruit production. Researchers have studied different methods for initiating early flower development in containerized plants. For example, researchers have attempted to place containerized plants in large coolers (without light) to initiate flower buds, but this has not been successful.

Many environmental conditions have been shown to affect strawberry plant growth and development during propagation. See, for example Durner, E. F., E. B. Poling, and E. A. Albregts [1987] "Early season yield responses of selected strawberry cultivars to photoperiod and chilling in a Florida winter production system" *J. Amer. Soc. Hort. Sci.* 112:53–56; Maas, J. L. [1986] "Photoperiod and temperature effects on starch accumulation in strawberry roots" *Adv. Strawberry Prod.* 5:22–24; Long, J. H. [1935] "Seasonal changes in nitrogen and carbohydrate content of the strawberry plant" *Proc. Amer. Soc. Hort. Sci.* 33:386–388 as well as dormancy Bringhurst, R. S., V. Voth and D. VanHook [1960] "Relationship of root starch content and chilling history to performance of California strawberries" *Proc. Amer. Soc. Hon. Sci.* 75:373–381; and Durner, E. F., J. A. Barden, D. G. Himelrick, and E. B. Poling [1984] "Photoperiod and temperature effects on flower and runner development in day-neutral, Junebearing, and Everbearing strawberries" *J. Amer. Soc. Hort. Sci.* 109:396–400.

BRIEF SUMMARY OF THE INVENTION

The subject invention concerns methods for enhancing flower induction in strawberry plants. More specifically, one embodiment of the subject invention provides a method for inducing flowering in strawberry plants by reducing the daytime temperature of the strawberry plants. In a preferred embodiment of the subject invention the daytime temperature may be reduced from about 30° C. to about 20° C. in order to induce flowering.

In a further embodiment of the subject invention, enhanced flower induction can be obtained according to the subject invention by reducing the amount of daylight (photoperiod) to which the strawberry plant is exposed. For example, if the photoperiod in a particular area is about 12 hours, then this can be reduced to a period of time, such as 6–10 hours, sufficient to enhance flower induction. In using this means to enhance flower induction, it is not necessary to reduce the temperature. Alternatively, with the reduced photoperiod the temperature may be reduced to a lesser extent than when a full photoperiod is used.

The optimal photoperiod and temperature can be readily determined by a person skilled in the art, having the benefit of the instant disclosure, for a particular strawberry plant species in a particular location.

DETAILED DISCLOSURE OF THE INVENTION

Advantageously, the method of the subject invention can be used to provide increased production of strawberries at the desirable peak period of the year by inducing flowering of the strawberry plant. This artificially controlled means of enhancing the flowering of the strawberry plant, advantageously, allows for increased strawberry production during the peak demand periods of the year.

In one embodiment of the subject invention, the daylight temperature of the strawberry plant is reduced to enhance the induction of flowering in the strawberry plant. The degrees and time adjustment can be readily determined by the strawberry plant grower for the various strawberry species grown. Containerized strawberry plants can either be subjected to artificially cooling the air or growing the plants at geographic locations in which the air temperature is conducive to flower initiation.

Alternatively, reducing the exposure time of the strawberry plant to daylight also can be done. Further, a combination of these means can be used to enhance flower induction.

In accordance with the subject invention, strawberry transplants can be grown at high temperatures (not conducive to flower formation) for approximately six to ten weeks. These plants can then be subjected to lower temperatures for flower initiation. Temperature and duration is dependent on variety and can be determined by the skilled artisan having the benefit of the instant disclosure. If flowers are formed early in transplant development they may interfere with transplant establishment. Containerized transplants conditioned for flower initiation can produce large quantities of high quality fruit. Early production attains a premium value and therefore justifies additional expense for conditioning plants.

In a preferred embodiment of the subject invention, strawberry plants are induced to flower by reducing the daytime temperature abruptly after a period of growth at temperatures which are sufficiently high such that flowering is not promoted. For example, strawberry plants may be grown for a period of several weeks at about 30° C. or higher after which time the daytime temperature can be reduced to 25° C. or lower. Preferably, the daytime temperature is reduced to about 15 to 20° C. The nighttime temperature may be maintained at about 30° C. or higher, or the nighttime temperature may also be reduced.

In a further embodiment of the subject invention, strawberry plants can be induced to flower by reducing the photoperiod to which the plants are exposed. Preferably, the reduction in photoperiod can be done abruptly. Thus, for example, plants which have been exposed to a photoperiod of 12 hours may have this photoperiod reduced to about 6–10 hours.

Both the reduction in photoperiod and the reduction in daytime temperature are preferably carried out in a controlled fashion such as in a greenhouse.

The subject invention also concerns a strawberry plant having enhanced flower induction produced by any of the methods, or combination thereof, described herein.

Following is an example which illustrates procedures for practicing the invention. This example should not be construed as limiting.

EXAMPLE 1

Early Induction of Flowering by Cold Daytime Treatment

Plug transplants were grown at four temperature regimes (20/30, 20/20, 30/30, 30/20° C. day/night) prior to transplanting. Plug transplants grown at 20° C. in the day flowered earlier than transplants grown at 30° C. daytime temperature.

It should be understood that the example and embodiments described herein are for illustrative purposes only and that various modifications or changes in light thereof will be suggested to persons skilled in the art and are to be included within the spirit and purview of this application.

What is claimed is:

1. A method for conditioning containerized, vegetative strawberry plants to induce early flowering upon transplantation, said method comprising:
    (a) growing said vegetative, containerized strawberry plants in a controlled-temperature environment for a first growing period of at least six weeks, under periodic light, and at a daytime temperature which reaches at least 30° C.;
    (b) growing said vegetative, containerized strawberry plants in a controlled-temperature environment for a second growing period under periodic light, after said first growing period, wherein said daytime temnerature is reduced to 25° C. or lower, thereby conditioning said vegetative, containerized strawberry plants for flower induction; and
    (c) transplanting said vegetative, conditioned strawberry plants, wherein said vegetative, conditioned strawberry plants are thereby induced to flower at a time of year that is not normally possible for the species of said strawberry plants in the absence of said conditioning.

2. The method, according to claim 1, wherein said method further comprises reducing the duration of each light period to which said plants are exposed during said second growing period compared to said first growing period.

3. The method according to claim 2, wherein the duration of each light period is reduced by at least fifty percent.

4. The method according to claim 2, wherein the duration of each light period is reduced to about six to ten hours.

5. The method according to claim 1, wherein said first growing period comprises about 6 weeks to about 10 weeks.

6. The method according to claim 1, wherein said method further comprises growing said strawberry plants at a nighttime temperature that reaches at least 30° C. during said first growing period.

7. The method according to claim 6, wherein said nighttime temperature reaches at least 30° C. during said first growing period and said second growing period.

8. The method according to claim 6, wherein said nighttime temperature is reduced during said second growing period compared to said first growing period.

9. The method according to claim 2, wherein the duration of each light period is reduced from about 12 hours in the first growing period to 6 to 10 hours in the second growing period.

10. The method according to claim 1, wherein said daytime temperature is reduced during the second growing period under periodic light, after said first growing period, to about 15° C. to 20° C.

11. The method according to claim 1, wherein said daytime temperature is reduced during the second growing period under periodic light, after said first growing period, to about 25° C.

12. The method according to claim 1, wherein said vegetative, conditioned strawberry plants are induced to flower in November or December.

13. The method according to claim 1, wherein said vegetative, conditioned strawberry plants are induced to flower in Florida, in November or December.

14. The method according to claim 1, wherein said conditioned strawberry plants are induced to flower at a time other than March or April.

15. The method according to claim 1, wherein said transplanting comprises removing said conditioned strawberry plants from their containers and placing said conditioned strawberry plants in conditions that are not conducive to flowering in the absence of said conditioning.

16. A method for conditioning containerized, vegetative strawberry plants to induce early flowering when subsequently transplanted, said method comprising:
    (a) growing said vegetative, containerized strawberry plants in a controlled-temperature environment for a first growing period of at least six weeks, under periodic light, and at a daytime temperature which reaches at least 30° C.; and
    (b) growing said vegetative, containerized strawberry plants in a controlled-temperature environment for a second growing period under periodic light, after said first growing period, wherein said daytime temperature is reduced to 25° C. or lower, thereby conditioning said vegetative, containerized strawberry plants to flower, upon transplantation, at a time of year that is not normally possible for the species of said strawberry plants in the absence of said conditioning.

* * * * *

UNITED STATES PATENT AND TRADEMARK OFFICE
CERTIFICATE OF CORRECTION

| | | |
|---|---|---|
| PATENT NO. | : 6,807,769 B2 | Page 1 of 1 |
| DATED | : October 26, 2004 | |
| INVENTOR(S) | : Eric B. Bish, Daniel Cantliffe and Craig Chandler | |

It is certified that error appears in the above-identified patent and that said Letters Patent is hereby corrected as shown below:

Column 3,
Line 54, "temnerature" should read -- temperature --.

Signed and Sealed this

Twenty-ninth Day of March, 2005

JON W. DUDAS
*Director of the United States Patent and Trademark Office*